United States Patent [19]

Lim et al.

[11] 4,322,311
[45] * Mar. 30, 1982

[54] PROCESS FOR PRODUCING CONTROLLED POROSITY MICROCAPSULES

[75] Inventors: Franklin Lim, Richmond; Richard D. Moss, Chester, both of Va.

[73] Assignee: Damon Corporation, Needham Heights, Mass.

[*] Notice: The portion of the term of this patent subsequent to Feb. 17, 1998, has been disclaimed.

[21] Appl. No.: 143,932

[22] Filed: Apr. 25, 1980

Related U.S. Application Data

[63] Continuation of Ser. No. 931,177, Aug. 4, 1978, abandoned, which is a continuation-in-part of Ser. No. 606,166, Aug. 20, 1975.

[51] Int. Cl.$^3$ .............................................. B01J 13/02
[52] U.S. Cl. ...................................... 252/316; 424/32; 424/85; 424/94; 424/DIG. 7
[58] Field of Search ............................ 252/316; 424/32

[56] References Cited

U.S. PATENT DOCUMENTS

| | | | |
|---|---|---|---|
| 3,429,827 | 2/1969 | Ruus | 252/316 |
| 3,577,515 | 5/1971 | Vandegaer | 252/316 X |
| 3,864,275 | 2/1975 | Kan et al. | 252/316 |
| 4,251,387 | 2/1981 | Lim et al. | 252/316 |

FOREIGN PATENT DOCUMENTS

| | | | |
|---|---|---|---|
| 873815 | 6/1971 | Canada | 252/316 |
| 1600988 | 9/1970 | France | 252/316 |

*Primary Examiner*—Richard D. Lovering
*Attorney, Agent, or Firm*—Kenway & Jenney

[57] ABSTRACT

A process for producing microcapsules of controlled porosity containing a chemically active core material. A core material such as a biologically active material and a first monomer in aqueous solution are emulsified in a hydrophobic solvent. A monomer complementary to the first and soluble in the continuous, hydrophobic phase of the emulsion is added to initiate interfacial polymerization about the aqueous droplets. During the course of the reaction, the affinity of the continuous phase for the first monomer is varied by adding a solvent to the continuous phase to vary its polarity. The continuous phase may be relatively nonpolar at the outset and a polar solvent may be added to increase its affinity for the first monomer, or it may be relatively polar at the outset and a nonpolar (or less polar) solvent may be added. This technique allows production of microcapsules having a selected pore size so that, for example, encapsulated material cannot escape, yet lower molecular weight materials can diffuse through the capsule wall.

23 Claims, No Drawings

PROCESS FOR PRODUCING CONTROLLED POROSITY MICROCAPSULES

REFERENCE TO RELATED APPLICATIONS

This application is a continuation of copending application Ser. No. 931,177 filed Aug. 4, 1978, now abandoned, which was a continuation-in-part of co-pending application Ser. No. 606,166, filed Aug. 20, 1975.

BACKGROUND OF THE INVENTION

In the above-noted copending application, the disclosure of which is incorporated herein by reference, a process for microencapsulating labile biological materials in a semipermeable membrane is disclosed. That process comprises an improvement in the well-known microencapsulation procedure known as interfacial polymerization, which involves forming an emulsion having an aqueous or hydrophilic discontinuous phase containing one of two complementary monomers and the material to be encapsulated and a hydrophobic continuous phase. When the complementary monomer is added to the emulsion, polymerization occurs at the interphase about the typically 5-200 micron diameter aqueous droplets.

In accordance with the invention of the above-mentioned application, easily denatured biological material such as enzymes, hemoglobin, antigens, antibodies and the like may be microencapsulated such that they retain their biological activity if, for example, the aqueous discontinuous phase is buffered with carbon dioxide to have a pH of between about 8 and 9, and if the second monomer is the continuous phase of the emulsion is added incrementally so that its concentration at any given time is maintained at a low level. Furthermore, the above-referenced application discloses that microcapsules of a selected, relatively uniform porosity (semipermeability) can be produced in a two-stage procedure wherein the interfacial polymerization is interrupted by removing raw, poorly formed, macroporous microcapsules from the emulsion, the microcapsules are washed, and then resuspended in a different solvent having a lower affinity for the aqueous phase bound first monomer than that of the original solvent. When a second portion of the second monomer is added to the new continuous phase, further polymerization occurs preferentially within the macroporous structure of the raw capsules, and strong, semipermeable membranes are produced.

By utilizing these and other teachings in the application, it is possible to immobilize high molecular weight biological materials such as enzymes and the like within a membrane having pores too small to allow passage of the encapsulated material yet small enough to allow diffusion of lower molecular weight materials such as the enzyme's substrate.

SUMMARY OF THE INVENTION

It has now been discovered that semipermeable or controlled porosity microcapsules of the type discussed above can be produced without the necessity of isolating the raw, poorly formed microcapsules and that it is possible to produce high quality microcapsules of controlled porosity simply by varying the solubility characteristics of the continuous phase of the emulsion during the course of the interfacial polymerization.

Thus, an emulsion is produced wherein the discontinuous phase comprises a hydrophilic liquid or water containing the material to be encapsulated, a carrier material such as albumin (optionally), and a portion of a first monomer to be used in forming the capsule membranes. The continuous phase of the emulsion comprises a water immiscible solvent which, in a first embodiment, is of relatively nonpolar character. When a second monomer capable of polymerizing with the first under the conditions which obtain in the emulsion is added to the continuous phase, interfacial polymerization begins. Because of the low affinity of the monomer and other components of the aqueous phase for the nonpolar continuous phase, diffusion of aqueous phase components and water into the continuous phase is slow. This behavior minimized side reactions between the phases such as hydrolysis of the second monomer, and provides time for a uniform formation of a capsular membrane framework. If the reaction is allowed to proceed to completion, poorly formed membranes are produced because the long reaction time results in appreciable hydrolysis of the second monomer (if it comprises, for example, a polyfunctional acid chloride), or substantially impermeable membranes result. However, in accordance with the invention, as the interfacial polymerization proceeds, a polar solvent which is miscible with the hydrophobic continuous phase is added to the emulsion to render the continuous phase increasingly more polar, thus increasing the affinity of the aqueous phase monomer for the continuous phase. This in turn promotes diffusion of the monomer into the continuous phase resulting in a membrane of controlled porosity.

In another embodiment, the continuous phase is polar at the outset, resulting in the formation of a macroporous, sponge-like, relatively thick membrane, and as the polymerization proceeds, nonpolar solvent is added to the emulsion so that the affinity of the first monomer for the continuous phase is reduced. This results in "patching" of the macroporous defects and enables the production of microcapsules having pores of a selected size range.

In accordance with another aspect of the invention, semipermeable microcapsules are produced using two polyfunctional amines in the aqueous discontinuous phase: a first amine of relatively high polarity, e.g., tetraethylene pentamine, and a second amine of lower polarity, e.g., hexane diamine. In this situation, the nature of the solvent system used for the continuous phase can be varied to sequentially draw the more polar and less polar monomers into the continuous phase. Thus, if the pentamine-diamine system mentioned above is employed, a continuous phase comprising cyclohexane and 1 or 2% chloroform will draw the pentamine from the aqueous droplets preferentially to the diamine for initial rapid deposition of capsular membrane framework. As the continuous phase is made more polar by the addition of more polar solvent (such as chloroform) and as the pentamine in the system is exhausted, diamine diffuses out through the polyamide network, reacting with additional quantities of diacid halide, and filling in macropores to complete the final details of the semipermeable membrane.

Accordingly, it is an object of the invention to provide a method of manufacturing microcapsules containing chemically active core materials wherein the microcapsule membranes have a relatively uniform degree of semipermeability, that is, have a pore size range such that encapsulated material cannot escape, yet lower molecular weight substances can freely pass.

Another object of the invention is to provide a microencapsulation procedure, the operability of which is based on solubility characteristics of the monomers and solvents involved and which accordingly may be practiced utilizing a variety of different polymer systems and different interfacial polymerization techniques.

Another object of the invention is to provide strong semipermeable microcapsules with membranes having pore sizes within a selected range.

Still another object of the invention is to provide an interfacial condensation technique which is operable at room temperature.

DESCRIPTION OF THE PREFERRED EMBODIMENT

The invention utilizes a novel variation in the well-known microencapsulation technique known as interfacial polymerization. Two mutually immiscible solvents are selected, one being hydrophobic, the other being hydrophilic or water. A polymer system is selected of the type wherein two different monomers undergo a polyaddition or polycondensation reaction to form polymer chains comprising alternating monomer units. The two reactive monomers must accordingly be at least di-functional, although other polyfunctional monomers may be employed to increase the cross-link density of the finally formed membrane. Since the process of the invention depends on the different solubility characteristics of the monomers selected for use in the system, i.e., on complementary monomers having differing polarities, it is necessary that the particular polymer system selected include a water soluble (hydrophilic) monomer and a relatively nonpolar hydrophobic monomer which may be solvated in water immiscible solvents.

In view of the foregoing, it will be appreciated that a number of polymer systems are useable in the process of the invention. Thus, while this specification deals primarily with a polyfunctional amine—polyfunctional acid halide polymer system, the invention may also be practiced with, for example, polyols and diacid or diacid halide systems to produce polyester membranes, diamine and diisocyanate systems to produce a polyurea, diols and acid halides to produce polycarbonates, multifunctional sulfonyl halides and diamines to produce polysulfonamides, and other well-known systems which react by polycondensation. Furthermore, polymer systems which react by polyaddition such as the type disclosed in U.S. Pat. No. 3,864,275 to Kan et al. are also within the scope of the invention. Thus, it will be within the skill of those in the art to utilize the solubility differences of the monomers of polymer systems such as polyfunctional amine epichlorohydrin or polyesters containing epoxy groups.

In the process of the invention, the material to be encapsulated and a first monomer such as a diamine are dissolved in a hydrophilic solvent, e.g., water, preferably together with an inert carrier material such as polyvinylpyrrolidone, dextran, polyethylene glycol, ficol, hemoglobin, or albumin. The carrier material is selected to provide a suitable environment for the reactions which the chemically active material to be encapsulated undergoes. Inert dyes may be included as a capsule marker if desired. This aqueous phase is then mixed with a water immiscible organic solvent and the two-phase system is emulsified, the hydrophobic solvent being the continuous phase. The size of the droplets determines the size of the microcapsule which will be produced. Emulsification may be accomplished by any of the well-known emulsification techniques such as, for example, using a blender, and will normally be accomplished with the aid of an emulsifying agent. Since the size of the droplets produced using any given technique will vary within a specific range, a filter may be used to separate oversized capsules made in any given run to minimize differences in capsule diameter. For a more detailed disclosure of methods for varying droplet size, reference should be made to *Artificial Cells*, Thomas M. S. Chang, Charles C. Thomas Publisher, Springfield, Ill., 1972, Chapter 2.

When droplets of a desired size have been produced, a second, hydrophobic solvent-soluble monomer capsule of forming a polymer with the first monomer by polycondensation or polyaddition is introduced into the emulsion. Polymerization occurs only at the interphase of the two phase system. If sufficient amounts of the second monomer are added to the emulsion and the reaction is allowed to proceed to completion, capsule membranes are produced which vary in porosity, strength, and thickness, and it is difficult or impossible to control the reaction so that microcapsules of a given porosity or membrane thickness are produced. In the case of the preferred diamine-diacid halide system, poorly formed capsules are produced because of hydrolysis of the diacid halides, which results in premature termination of the forming polymer chains.

The nature of the membrane depends primarily on the nature of the interphase and on the affinity of the interphase for the first monomer contained within the aqueous droplets. Thus, since the first monomer must necessarily be of polar character, its diffusion rate depends on the degree of polarity of the continuous phase. If the continuous phase has a low porosity, the diffusion rate is slow and the interphase is relatively thin. Accordingly, the complementary monomers meet and form a thin membrane about the aqueous droplets. On the other hand, if at the outset the continuous phase is of polar character, the diffusion rate is increased, the diffusion path lengthens, and a macroporous, sponge-like, relatively thick membrane network forms.

In accordance with a first aspect of the invention, the solubility characteristics of the continuous phase are varied by admixing a second solvent with the continuous phase during the course of the interfacial polymerization. Thus, when a relatively nonpolar continuous phase is initially used, diffusion of aqueous phase components into the interphase is slow. This minimizes harmful side reactions such as hydrolysis and allows more time for a uniform capsule membrane network to form. As the polymerization continues and membranes take shape, the diffusion process slows down further. If the organic phase is now made more polar by the addition of a highly polar organic solvent, preferably either in increments or by controlled continuous injection, the rate of diffusion can be maintained at suitable levels to complete the microencapsulation.

Conversely, the continuous phase can initially comprise a relatively polar solvent. This promotes formation of a network of polymer formed along the length of the diffusion path. Thereafter, the solubility characteristics of the continuous phase are altered by the addition of quantities of highly nonpolar materials such as pure cyclohexane. This causes a slow-down in the diffusion rate, and results in preferential formation of polymer within the interstices of the polymer network.

A further refinement in the process set forth above involves the use of two monomers in the discontinuous phase. Both monomers are necessarily water soluble and thus quite polar, but they are selected to differ in polarity as much as possible while still being water soluble. In one important embodiment, the less polar component is hexane diamine and the more polar component is tetraethylenepentamine preferable present in the aqueous phase at a ratio of pentamine to diamine of about 0.05. If a continuous phase such as a solution of 1%–2% chloroform in hexane is employed, the pentamine diffuses into the interphase more rapidly than the diamine, resulting in initial rapid deposition of a membrane framework. After sufficient time has elapsed for the pentamine to react, the continuous phase is made more polar by the addition of pure chloroform, e.g., incrementally, and the final details of the membrane deposition are completed.

Within the context of the foregoing process, it is possible to microencapsulate chemically active materials such as labile biological materials without deactivation. Thus, as disclosed in copending application Ser. No. 606,166, the pH of the aqueous phase may be maintained between about 8 and 9 by using a buffer such as carbon dioxide. In the polyfunctional amine system disclosed above, this means that the diffusing monomer will be a carbonate. Also, since the second, continuous phase solvated monomer will frequently be capable of deactivating easily denatured substances selected for encapsulation, and since exposure of the second monomer to water often results in hydrolysis side reactions which terminate the formation of polymer chains, the second monomer is normally added in increments over the duration of the polymerization so that its concentration at any given time is low. Also, with some labile biological materials, it is possible to incorporate a hypertonic saline solution in the continuous phase to promote water retention.

In the preferred polyamide polymer system, the first monomer incorporated in the discontinuous phase may be, for example, 1, 6 hexane diamine, lysine 2, 2' diamino 2, 2' biphenyl disulfonic acid, 4, 4' diamino stilbene 2, 2' disulfonic acid, 2, 5 diaminobenzenesulfonic acid, carbonates of the foregoing amines, and mixtures thereof. The second, continuous-phase solvated monomer may be, for example, sebacyl halide, e.g., chloride, terephthaloyl halide, and mixtures thereof.

The invention will be further understood from the following nonlimiting examples.

EXAMPLE 1

One and one-half ml of an aqueous carrier solution comprising polyvinylpyrrolidone, albumin, and 250 $\mu$l of antisera to thyroxine were mixed with 50 $\mu$l of 0.5 M tetraethylene pentamine carbonate (pH=8.2–8.6). The aqueous phase was then added to 15 ml of cyclohexane containing 3%–6% ARLACEL (sorbitan oleate) as an emulsifier. The two-phase system was emulsified by means of a magnetic stirring bar, and as stirring continued, one 2 ml portion of a 4:1 (v/v) cyclohexane-chloroform solution containing 0.1 mg/ml terephthaloyl chloride was added to initiate polymerization.

Sixty seconds later, another 0.8 ml of the terephthaloyl chloride solution was added. After 60 more seconds, 0.5 ml of pure chloroform were added to increase the affinity of the continuous phase for the polyfunctional amines; then, at 30 second intervals, three additional 0.5 ml increments of chloroform were added.

After a total reaction time of four minutes, the emulsion was gently centrifuged and the supernatant liquid discarded. The microcapsules were washed with pure cyclohexane and a 50% aqueous TWEEN-20 solution (sorbitan monolaurate) buffered to neutral pH with 0.3 M $NaHCO_3$.

The foregoing procedure results in capsules having a pore size large enough to allow free passage of thyroxin, which has a molecular weight of about 777 daltons, yet too small to allow leakage of antibody from the interior of the capsules.

EXAMPLE 2

Two and one-half ml of an aqueous carrier solution comprising polyvinylpyrrolidone, albumin, $Na_2CO_3$/$NaHCO_3$ buffer, and 0.3 ml of glucose oxidase were mixed with 1.2 ml of hexane-diamine carbonate (2.5M; pH 8.4–8.6). This aqueous phase was then added to 30 ml of a mixed organic solvent consisting of 50 parts cyclohexane, 5 parts chloroform, and containing 3%–5% sorbitan oleate as an emulsifier. The two-phase system was emulsified by means of an emulsifying stirring probe.

While stirring, 2.6 ml of the terephthaloyl chloride solution of example 1 was added to initiate polymerization. Another 0.8 ml aliquot of the terephthaloyl chloride solution was added 30 seconds later. This was followed by the addition of four 5.0 ml volumes of cyclohexane, spaced at 30 second intervals.

At the end of 3.5 minutes of total polymerization reaction time, the reaction was terminated and the microcapsules harvested as set forth in Example 1. Glucose oxidase was retained within the capsules, yet glucose (mw $\approx$ 180) diffused through the membranes.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

We claim:

1. A process for encapsulating a chemically active material within a membrane of a selected porosity, said process comprising the steps of:

A. solubilizing said material in water together with a water soluble first monomer selected from the group consisting of multifunctional amines, polyols, and diols to produce an aqueous phase;

B. emulsifying the aqueous phase in a continuous phase comprising a hydrophobic solvent;

C. adding a substantially water insoluble second monomer selected from the group consisting of multifunctional acid halides, diacids, diisocyanates, and multifunctional sulfonyl halides to said emulsion to produce porous membranes comprising a polymer formed by interfacial polymerization about the members of the aqueous, discontinuous phase, said first and second monomers having differing solubility characteristics and being capable of reacting by polycondensation or polyaddition;

D. adding hydrophobic solvent-miscible material to said hydrophobic solvent to vary the polarity of said continuous phase, thereby to alter the affinity of said first monomer for the continuous phase during the polymerization of said first and second monomers;

E. allowing said first and second monomers to further polymerize at the interface of the altered continuous phase; and F. quenching the interfacial polymerization when microcapsules of the selected porosity have been produced.

2. The process as set forth in claim 1 wherein the hydrophobic solvent is relatively nonpolar and the hydrophobic solvent-miscible material is a polar solvent which increases the affinity of the first monomer for the continuous phase.

3. The process as set forth in claim 1 wherein the hydrophobic solvent is a relatively polar solvent and the hydrophobic solvent-miscible material is a nonpolar solvent which decreases the affinity of the first monomer for the continuous phase.

4. The process as set forth in claim 1 wherein the first monomer is a polyfunctional amine and the second monomer is a polyfunctional acid halide.

5. The process as set forth in claim 4 wherein the amine is selected from the group consisting of 1,6 hexane diamine, lysine, 4,4' diamino 2,2' biphenyl disulfonic acid, 4,4' diamino stilbene, 2,2' disulfonic acid, and 2,5 diaminobenzenesulfonic acid.

6. The process as set forth in claim 4 wherein the acid halide is selected from the group consisting of sebacyl chloride and terephthaloyl chloride.

7. The process as set forth in claim 4 wherein the first monomer includes a portion of tetraethylene pentamine.

8. The process as set forth in claim 4 wherein the hydrophobic solvent is cyclohexane and the hydrophobic solvent-miscible material is chloroform.

9. The process as set forth in claim 1 wherein a carrier material for the chemically active material is included in the aqueous phase.

10. The process as set forth in claim 9 wherein the carrier material is selected from the group consisting of polyvinylpyrrolidone, dextran, polyethylene glycol, ficol, hemoglobin, and albumin.

11. The process as set forth in claim 1 wherein the second monomer is added to the emulsion incrementally as the interfacial polymerization proceeds.

12. The process as set forth in claim 1 wherein the chemically active material is a labile biological material.

13. The process as set forth in claim 1 wherein the hydrophobic solvent-miscible material is added incrementally as the interfacial polymerization proceeds.

14. A process for encapsulating a chemically active material within a membrane of a selected porosity, said process comprising the steps of:

A. solubilizing said material in water together with a polyfunctional amine to produce an aqueous phase;

B. emulsifying the aqueous phase in a continuous phase comprising a nonpolar hydrophobic solvent;

C. adding a substantially water insoluble diacid halide to said emulsion to produce a membrane framework comprising a polymer about the surface of the members of the discontinuous aqueous phase by interfacial polymerization;

D. adding a hydrophobic solvent-soluble polar solvent to the emulsion to increase the affinity of the poly-functional amine for the continuous phase thereby to promote diffusion of said poly-functional amine into the framework;

E. allowing an additional quantity of said poly-functional amine to react with additional quantities of said diacid halide within said framework; and F. quenching the interfacial polymerization when microcapsules of the selected porosity have been produced.

15. The process as set forth in claim 14 wherein the diacid halide is a diacid chloride selected from the group consisting of sebacyl chloride and terephthaloyl chloride, and the polyfunctional amine is selected from the group consisting of 1, 6 hexane diamine, tetraethylene pentamine, lysine, 4, 4' diamino 2, 2' biphenyl disulfonic acid, 4, 4' diamino stilbene 2, 2' disulfonic acid, 2, and 5 diaminobenzenesulfonic acid.

16. The process as set forth in claim 14 wherein the hydrophobic solvent is cyclohexane and the polar solvent is chloroform.

17. The process as set forth in claim 14 wherein the polar solvent is added to the emulsion incrementally as the interfacial polymerization proceeds.

18. The process as set forth in claim 14 wherein additional quantities of the diacid halide are incrementally added to the emulsion as the interfacial polymerization proceeds.

19. The process as set forth in claim 14 wherein the chemically active material is a labile biological material.

20. The process as set forth in claim 14 wherein a carrier material for the chemically active material is included in the aqueous phase.

21. The process as set forth in claim 20 wherein the carrier material is selected from the group consisting of polyvinylpyrrolidone, dextran, polyethylene glycol, ficol, hemoglobin, and albumin.

22. The process as set forth in claim 14 wherein both a pentamine and a diamine are solubilized in the aqueous phase.

23. The process as set forth in claim 22 wherein the mole ratio of pentamine to diamine is on the order of 0.05.

* * * * *